US006518317B1

(12) United States Patent
Sagawa et al.

(10) Patent No.: US 6,518,317 B1
(45) Date of Patent: Feb. 11, 2003

(54) ANTIVIRAL AGENTS

(75) Inventors: Hiroaki Sagawa, Otsu (JP); Nobuto Koyama, Otsu (JP); Hideto Chono, Otsu (JP); Kazutoh Takesako, Otsu (JP); Ikunoshin Kato, Otsu (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

(21) Appl. No.: 09/367,185

(22) PCT Filed: Feb. 26, 1998

(86) PCT No.: PCT/JP98/00816

§ 371 (c)(1),
(2), (4) Date: Aug. 9, 1999

(87) PCT Pub. No.: WO98/41196

PCT Pub. Date: Sep. 24, 1998

(30) Foreign Application Priority Data

Mar. 17, 1997 (JP) ............................................. 9-082376
Jul. 22, 1997 (JP) ............................................. 9-210193
Aug. 8, 1997 (JP) ............................................. 9-225533

(51) Int. Cl.⁷ .................... A61K 31/122; A61K 31/047; A61P 31/14; A61P 31/12; A61P 31/18
(52) U.S. Cl. .................... 514/690; 514/894; 514/729
(58) Field of Search .................... 514/690, 894, 514/729

(56) References Cited

U.S. PATENT DOCUMENTS

| 5,149,711 A | 9/1992 | Hazato et al. ............... 514/548 |
| 6,087,401 A | 7/2000 | Koyama et al. ............. 514/690 |

FOREIGN PATENT DOCUMENTS

| EP | 0 974 347 | 1/2000 |
| EP | 0 978 277 | 2/2000 |
| EP | 0 978 278 | 2/2000 |
| EP | 1 008 345 | 6/2000 |
| WO | 98/13328 | 4/1998 |

OTHER PUBLICATIONS

European Search Report.
* related to pending U.S. Patent Application Serial No. 09/367,163.
**related to pending U.S. Patent Application Serial No. 09/380,239.
***related to pending U.S. Patent Application Serial No. 09/423,883.
Wilson et al., Ann. N.Y. Acad. Sci., vol. 804, pp. 276–283 (abstract).
Ahmad et al., "On the formation of reductic acid from pentoses or huxuronic acids", Carbohydrate Research (1993), 247, pp. 217–222.
Cocu et al., "Research on the series of cyclitols XLIV. Synthesis of cyclose derivatives of cyclopentane", Helvita Chimica Acta (1972), 55(8), pp. 2838–2844.
Translation of Japanese Patent Publication (Kokai) No. Sho–50–70597.

*Primary Examiner*—Edward J. Webman
*Assistant Examiner*—Helen Nguyen
(74) *Attorney, Agent, or Firm*—Kennedy Covington Lobdell & Hickman, LLP

(57) ABSTRACT

An antiviral agent which is characterized in containing at least one compound selected from a group consisting of 4,5-dihydroxy-2-cyclopenten-1-one represented by the following formula [I] and an optically active substance and a salt thereof as an effective component.

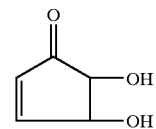

10 Claims, 7 Drawing Sheets

ANTIVIRAL AGENTS

TECHNICAL FIELD OF THE INVENTION

The present invention relates to pharmaceuticals, foods and beverages which are useful to pathogenic organisms due to their antiviral action.

PRIOR ART

In the antiviral action, there will be an action of inducing the resisting ability to virus such as inhibition of infection of virus to cells, inhibition of multiplication of virus in the infected cells, and the like, an action or selectively killing the cells which are infected by virus, and an action of inactivating (i.e., eliminating the infecting ability of) the virus itself.

There is a neutralizing antibody as a substance which has an action of inactivating the virus itself while there is vaccine as a means for inducing such an antibody. However, although the induction of the antibody by administration of vaccine is effective in preventing the infection of virus, effective therapeutic methods using antibody are rarely available at present. In addition, there is no effective therapeutic method in which virus is directly inactivated by pharmaceuticals.

With regard to action of inducing a resisting ability to virus, there will be inhibition of replication of genome of virus, inhibition of transcription of gene of virus, inhibition of synthesis of protein of virus, inhibition of folding of protein of virus, and the like. In inducing such actions, there will be suppression of activity or expression of transcription factor in the cell, suppression of activity or expression of transcription factor derived from virus, induction of heat shock proteins, and the like. An example of the substances which are capable of inducing such an action is prostaglandin.

Examples of the agents which selectively kill the cells which are infected by virus are acyclovir, ganciclovir, sorivudine, and the like which have been used as drugs against herpes virus.

PROBLEMS TO BE SOLVED BY THE INVENTION

Against virus, it is more effective to cope with by means of a synergistic action than by means of a single action. For example, even when a substance which selectively kills the virus-infected cells is administered, it is very difficult to completely eliminate the virus because, until the infected cells are killed, new virus is generated and other cells are infected by that. On the other hand, even when a substance which has an action of inducing a resisting ability to virus is administered, it is not possible to eliminate the infected cells.

An object of the present invention is to develop the compounds which have a function of inducing a resistance to virus into cells and a function of selectively killing the virus-infected cells and to offer pharmaceuticals such as antiviral agent, agent for improving the hepatic functions, agents for inducing heat shock proteins, agents for preventing the carcinogenesis by oncogene, agents for preventing the chemical carcinogenesis, and the like and antiviral foods or beverages wherein the above-mentioned compound is contained.

MEANS TO SOLVE THE PROBLEMS

The present inventors have conducted an intensive study for achieving such an object and have found that, when cells are treated with a compound which has a function of inducing a resistance to virus and of selectively killing the cells infected by virus, said virus-infected cells are selectively damaged and, therefore, amount of the virus which is generated until death of said cells decreases and that, since the cells which are not yet infected by virus acquire a resistance to virus due to administration of the compound, growth of the virus is suppressed even if it is newly infected. In other words, it has been found that the compound which has a function of inducing a resistance to virus into cells and of selectively killing the cells infected by virus is extremely effective for elimination of virus such as human AIDS virus or hepatitis C virus.

The function of the compound used in the present invention for inducing a resistance to virus into the cells can be measured by treating the compound to the cells prior to infection of virus followed by using inhibition of infection of virus to the cells, inhibition of replication of genome of virus, inhibition of transcription of gene of virus, inhibition of synthesis of protein of virus, inhibition of folding of protein of virus, and the like as the indexes or the yardsticks.

Further, the function of selectively killing the cells which are infected by virus can be measured by comparing the survival rate of the virus-infected cells with that of the uninfected cells.

There is absolutely no limitation for the compound having a function of inducing a resistance to virus into cells and also of selectively killing the cells infected by virus so far as said compound has both of those functions.

Now the present inventors have found 4,5-dihydroxy-2-cyclopenten-1-one represented by the formula [I] (hereinafter, just referred to as "the cyclopentenone") or an optically active compound or a salt thereof as the compound having a function of inducing a resistance to virus into cells and also of selectively killing the cells infected by virus whereupon the present invention has been achieved.

Outline of the present invention is that the first feature of the present invention relates to an antiviral agent which is characterized in containing at least one compound selected from a group consisting of 4,5-dihydroxy-2-cyclopenten-1-one represented by the following formula [I] and an optically active substance and a salt thereof as an effective component.

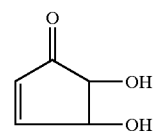

[I]

The second feature of the present invention relates to antiviral food or antiviral beverage which is characterized in containing at least one compound selected from a group consisting of 4,5-dihydroxy-2-cyclopenten-1-one represented by the formula [I] and an optically active substance and a salt thereof as an effective component.

In a preferred embodiment of the present invention, examples of the virus are human AIDS virus and hepatitis C virus. Examples of the antiviral agent are antiviral agent for human being, antiviral agent for non-human animals (such as antiviral agent for domestic animals, domestic fowls, fish or shrimps) and antiviral agent for plants.

EMBODIMENTS OF THE INVENTION

Figure 1:
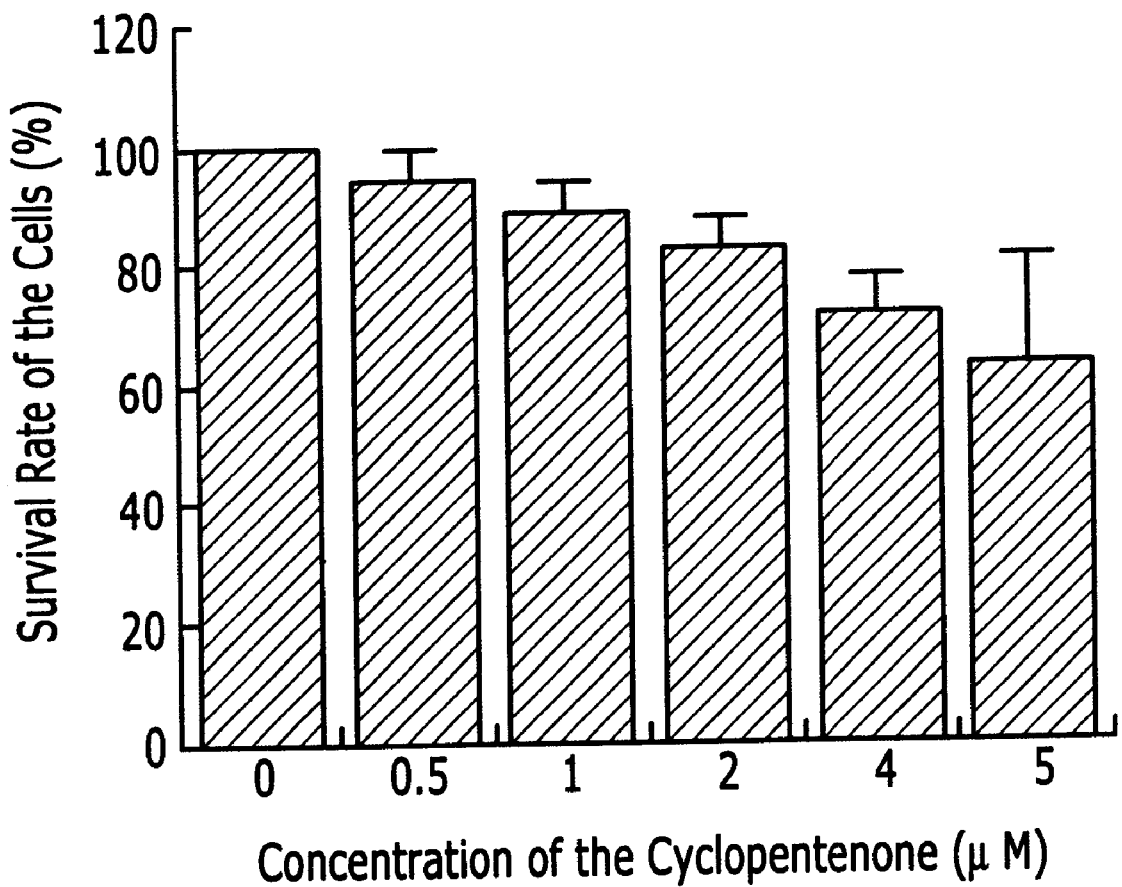
FIG. 1 is a graph showing the relation between the concentration of the cyclopentenone and the survival rate when CEM-SS cells are used.

The cyclopentenone represented by the formula [I] used in the present invention covers both isomers where the configurations of hydroxyl groups at 4- and 5-positions are cis and trans. In the present invention, any of cis-cyclopentenone, trans-cyclopentenone and a mixture of cis- and trans-cyclopentenone may be used. It is also possible to use optically active substances thereof. cis-Cyclopentenone may be prepared by a chemical synthesis [Helvetica Chimica Acta, volume 55, pages 2838–2844 (1972)]. trans-Cyclopentenone may be prepared either by a chemical synthesis [Carbohydrate Res., volume 247, pages 217–222 (1993)] or by heating uronic acid such as glucuronic acid, uronic acid derivative such as glucuronolactone or a substance containing the same (refer to PCT/JP97/03052). In the present invention, it is also possible to use such a heated product or partially purified product or purified product thereof.

For example, when D-glucuronic acid is used as a uronic acid and its 1% solution is heated at 121° C. for four hours, the cyclopentenone is produced in the heat-treated substance. The cyclopentenone in this heat-treated substance is extracted with a solvent and the extract is concentrated. Then, this concentrated extract is separated by means of a silica gel column chromatography, the eluted cyclopentenone fraction is concentrated, the cyclopentenone is extracted with chloroform from the concentrate and the extract of the concentrate is subjected to a normal phase column chromatography whereupon the cyclopentenone in the heat-treated substance is isolated.

Physical property of the cyclopentenone will be given as hereunder. Incidentally, a mass spectrometric analysis of the cyclopentenone was conducted using a mass spectrometer DX302 (manufactured by Nippon Denshi). Further, measurement of an NMR using heavy chloroform as a solvent was conducted by JNM-A 500 (manufactured by Nippon Denshi). Specific rotation was measured by a DIP-370 polarimeter (manufactured by Nippon Bunko); ultraviolet absorption spectrum was measured by a UV-2500 spectrophotometer (manufactured by Shimadzu); and infrared absorption spectrum (IR) was measured by an FTIR-8000 infrared spectrophotometer (manufactured by Shimadzu).

MS m/z 115 [M+H]$^+$; $^1$H-NMR (CDCl$_3$): δ 4.20 (1H, d, J=2.4 Hz, 5-H), 4.83 (1H, m, 4-H), 6.30 (1H, dd, J=1.2, 6.1 Hz, 2-H), 7.48 (1H, dd, J=2.1, 6.1 Hz, 3-H).

Incidentally, the chemical shift value of the $^1$H-NMR was given on a basis that the chemical shift value of CHCl$_3$ was 7.26 ppm.

Optical rotation: $[\alpha]_D^{20}$ 0° (c 1.3,. water); UV: $\lambda_{max}$ 215 nm (water); IR (KBr method): absorptions were noted at 3400, 1715, 1630, 1115, 1060, 1025 cm$^{-1}$.

When the isolated cyclopentenone is subjected to an optical resolution, (−)-4,5-dihydroxy-2-cyclopenten-1-one and (+)-4,5-dihydroxy-2-cyclopenten-1-one are obtained. It goes without saying that the cyclopentenone obtained by a synthetic method can be subjected to an optical resolution as well.

For example, the cyclopentenone is dissolved in ethanol. To this ethanolic solution is further added hexane/ethanol (94/6) to prepare a cyclopentenone solution. The cyclopentenone can be optically resolved when this sample solution is subjected to an HPLC using, for example, a Chiral PackAS (manufactured by Daicel Chemical Industries) under such a condition that the column temperature was 40° C. and the mobile phase was hexane/ethanol (94/6).

Optical rotation of the optically resolved (−)-trans-4,5-dihydroxy-2-cyclopenten-1-one [hereinafter, referred to as (−)-cyclopentenone] is $[\alpha]_D^{20}$ −105° (c 0.30, ethanol) while that of the optically resolved (+)-trans-4,5-dihydroxy-2-cyclopenten-1-one [hereinafter, referred to as (+)-cyclopentenone] is $[\alpha]_D^{20}$ +104° (c 0.53, ethanol). Incidentally, the optical rotation was measured by the above-mentioned polarimeter of the type DIP-370 (manufactured by Nippon Bunko).

After that, each of (−)-cyclopentenone and (+)-cyclopentenone was subjected to structural analysis by means of mass analysis and nuclear magnetic resonance (NMR), measurement of UV absorption spectrum and measurement of infrared absorption spectrum by the method mentioned already. As a result, both optically active substances showed the same result as that of the cyclopentenone before the optical resolution.

Each of the optically resolved (−)-cyclopentenone and (+)-cyclopentenone was converted to a p-dimethylaminobenzoyl derivative, the circular dichroism spectrum (CD) was measured using a circular dichroism dispersimeter of type J-720 (manufactured by Nippon Bunko) and the result was applied to a dibenzoate chirality rule [J. Am. Chem. Soc., volume 91, pages 3989–3991 (1969)] to determine the configuration.

Figure 6:
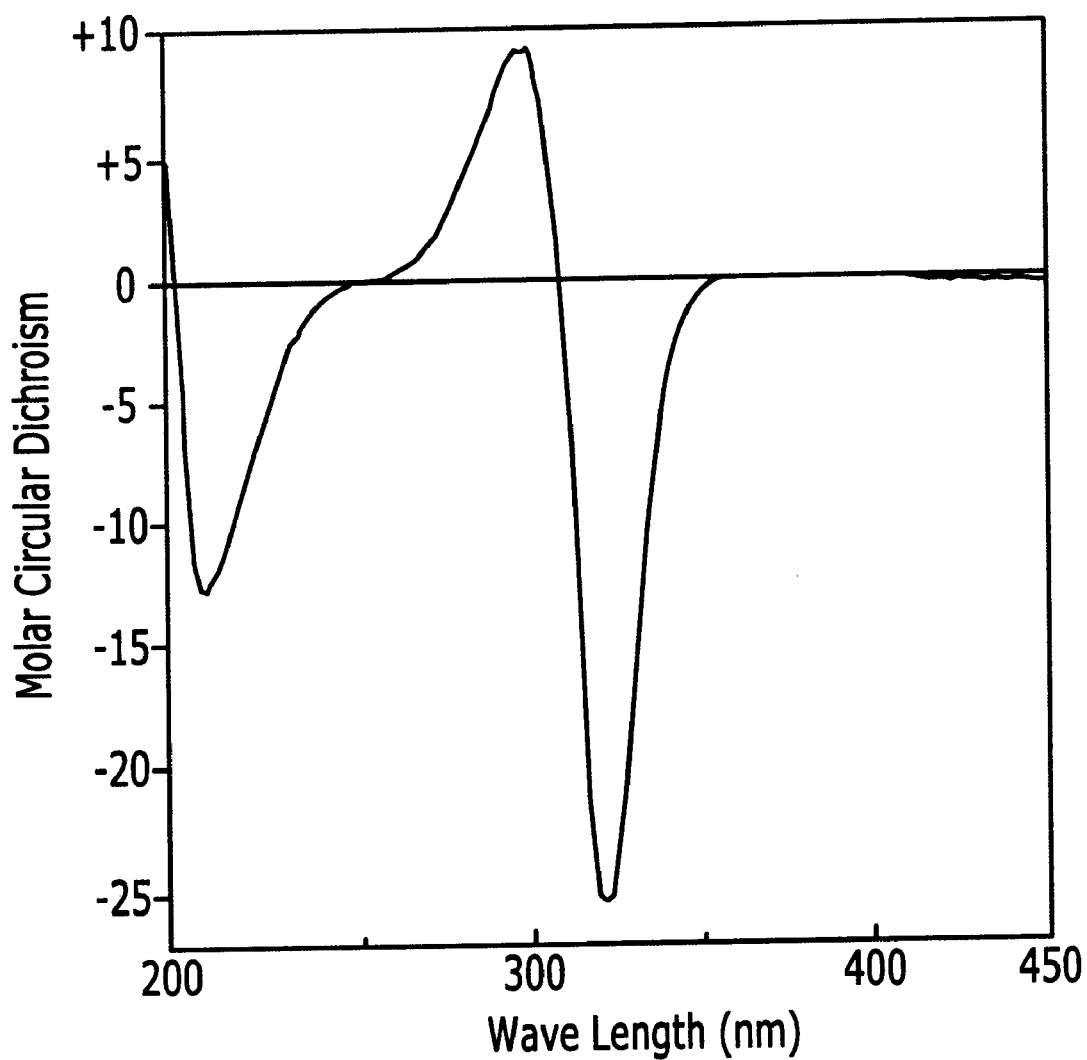
FIG. 6 shows a CD of p-dimethylaminobenzoyl derivative of (−)-cyclopentenone and a stereostructure of (−)-cyclopentenone.
Figure 6:
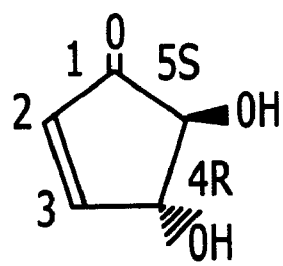

CD of p-dimethylaminobenzoyl derivative of (−)-cyclopentanone and stereostructure of (−)-cyclopentenone are shown in FIG. 6. In the drawing, the ordinate indicates molar circular dichroism while the abscissa indicates wavelength (nm). Incidentally, the above stereostructure is given hereunder as the formula [II]

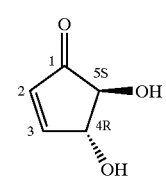

Figure 7:
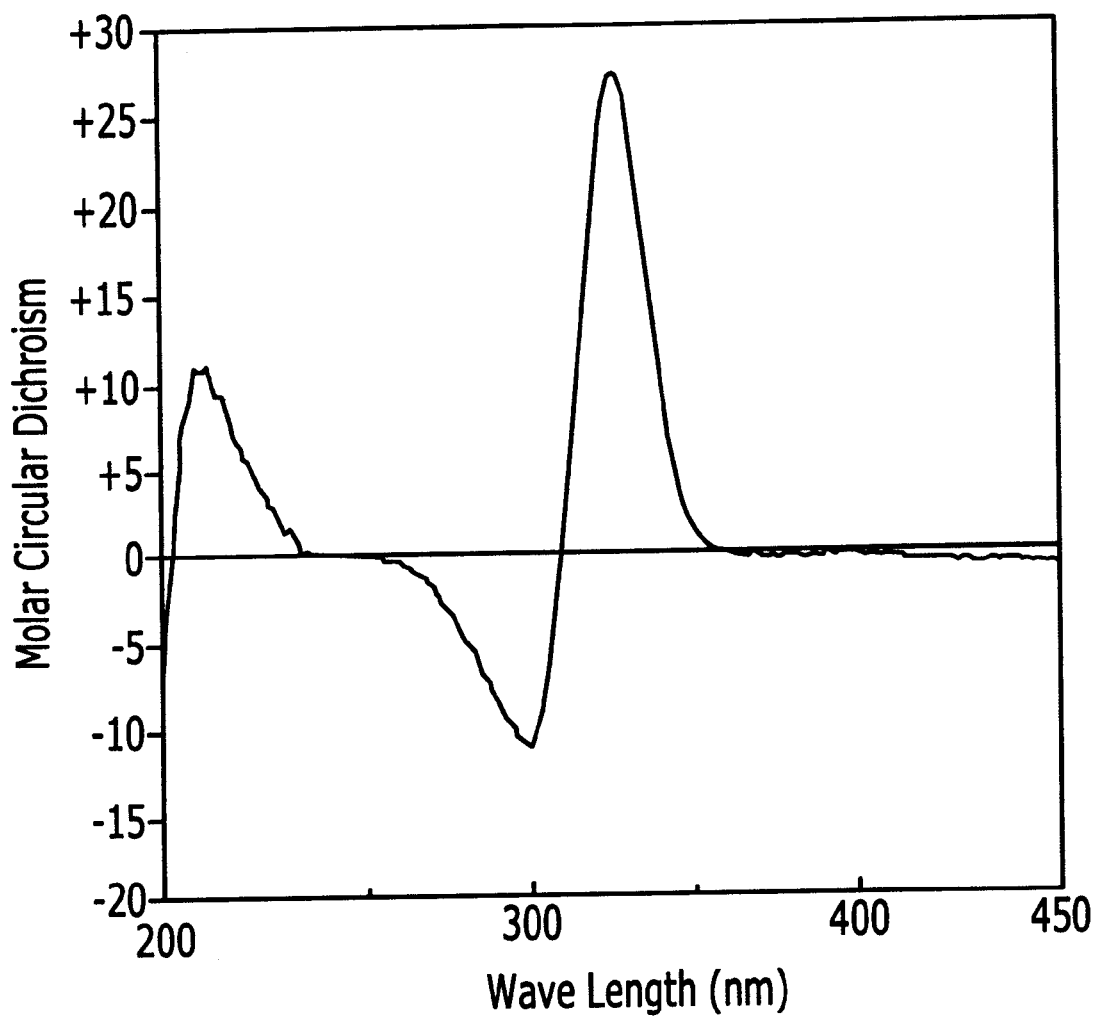
FIG. 7 shows a CD of p-dimethylaminobenzoyl derivative of (+)-cyclopentenone and a stereostructure of (+)-cyclopentenone.
Figure 7:
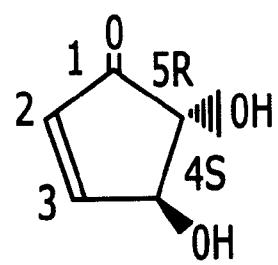

CD of p-dimethylaminobenzoyl derivative of (+)-cyclopentanone and stereostructure of (+)-cyclopentenone are shown in FIG. 7. In the drawing, the ordinate indicates molar circular dichroism while the abscissa indicates wave length (nm). Incidentally, the above stereostructure is given hereunder as the formula [III]:

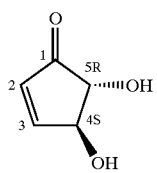

As shown in FIG. 6, FIG. 7, formula [II] and formula [III], the (−)-cyclopentenone is (−)-(4R,5S)-trans-4,5-dihydroxy-2-cyclopenten-1-one while the (+)-cyclopentenone is (+)-(4S,5R)-trans-4,5-dihydroxy-2-cyclopenten-1-one.

The above-mentioned cyclopentenones or an optically active substance thereof may be manufactured by any method, i.e. they may be manufactured by a method disclosed in this specification or by means of chemical synthesis; and trans- and cis-cyclopentenone or a mixture thereof may be used in the present invention as well. Naturally, an optically active substance of cyclopentenones obtained by a chemical synthetic method is also included in an optically active substance disclosed in the present invention.

Examples of the salt of the cyclopentenone or optically active substance thereof are pharmaceutically acceptable salts and they may be prepared by known converting methods.

The compound which is used in the present invention having a function of inducing a resistance to virus into cells and also having a function of selectively killing the cells infected by virus such as, for example, the cyclopentenone, an optically active substance or a salt thereof has an antiviral action and it is now possible to prepare an antiviral agent using at least one compound selected from the above as an effective component.

That is, the compound having a function of inducing a resistance to virus into cells and also having a function of selectively killing the cells infected by virus is used as an effective component and is made into a pharmaceutical preparation by compounding with known pharmaceutical carriers, it is now possible to prepare an antiviral agent. Generally, at least one of the compound selected from the compound having a function of inducing a resistance to virus into cells and also having a function of selectively killing the cells infected by virus such as, for example, the cyclopentenone, an optically active substance or a salt thereof is compounded with a pharmaceutically acceptable liquid or solid carrier and, if necessary, solvent, dispersing agent, emulsifier, buffer, stabilizer, filler, binder, disintegrating agent, lubricant, and the like are added thereto to give an antiviral agent which may be in solid such as tablets, granules, diluted powders, powders, capsules, and the like or in liquid such as solutions, suspensions, emulsions, and the like. Further, this may be in a dry preparation which can be made into liquid by adding an appropriate carrier before use.

The pharmaceutical carrier may be selected depending upon the above-mentioned mode of the administration and form of the preparation. In the case of oral preparations, starch, lactose, sugar, mannitol, carboxymethyl cellulose, corn starch, inorganic salts, and the like may be used. In the manufacture of oral preparations, binders, disintegrating agents, surface-active agents, lubricants, fluidity promoters, taste-correctives, coloring agents, flavors, and the like may be further compounded therewith.

On the other hand, in the case of parenteral preparations, they may be prepared by common methods where at least one of the compound selected from the compound having a function of inducing a resistance to virus into cells and also having a function of selectively killing the cells infected by virus such as, for example, the cyclopentenone, an optically active substance or a salt thereof which is an effective component of the present invention is dissolved or suspended in a diluent such as distilled water for injection, physiological saline solution, aqueous solution of glucose, vegetable oil for injection, sesame oil, peanut oil, soybean oil. Corn oil, propylene glycol, polyethylene glycol, and the like followed, if necessary, by adding bactericides, stabilizers, isotonic agents, analgesics, and the like thereto.

The antiviral agent of the present invention is administered by an appropriate route depending upon the form of the preparation. There is no particular limitation for the method of administration as well and it may be administered by means of oral use, external use and injection. Injection preparations are administered, for example, intravenously, intramuscularly, subcutaneously, intracutaneously, and the like while preparations for external use include suppositories, and the like.

The dose as the antiviral agent is not particularly specified by may be appropriately determined depending upon the dosage form, administration method, purpose of the use and age, body weight, conditions, and the like of the patient. Usually, however, the amount of at least one of the compound selected from the compound having a function of inducing a resistance to virus into cells and also having a function of selectively killing the cells infected by virus such as, for example, the cyclopentenone, an optically active substance or a salt thereof contained in the preparation for an adult is 0.1 μg–20mg/kg per day. As a matter of course, the dose may vary depending upon various factors and, therefore, the dose less than the above-mentioned one may be sufficient in some cases while, in other cases, the dose more than the above may be necessary. The agent of the present invention may be administered orally as it is and, further, the agent may be taken daily after adding to common food and/or beverage as well. Furthermore, the compound having a function of inducing a resistance to virus into cells and also having a function of selectively killing the cells infected by virus such as, for example, the cyclopentenone, an optically active substance or a salt thereof may be used as a material for the antiviral agent, antiviral food or beverage.

The compound having a function of inducing a resistance to virus into cells and also having a function of selectively killing the cells infected by virus such as, for example, the cyclopentenone, an optically active substance or a salt thereof used the present invention has antiviral activity against DNA virus, RNA virus, retrovirus and viroid.

Accordingly, it may be used as antiviral agent for human being, antiviral agent for non-human animals such as that effective to viral diseases (e.g. for domestic animals, domestic fowls and cultured animals such as fish and shrimp), antiviral agent for plants such as that for viral diseases of agricultural and horticultural products (e.g. flowers and vegetables) and antiviral agent for useful animate things.

Examples of DNA virus infecting the animals are pox virus, herpes virus, adenovirus, hepatitis B virus, papilloma virus, polyoma virus, Epstein-Barr virus and baculovirus while an example of DNA virus infecting the plants is cauliflower mosaic virus. Examples of RNA virus infecting the animals are rotavirus, rubella virus, Japanese encephalitis virus, dengue virus, Newcastle disease virus, measles virus, mumpus virus, distemper virus, influenza virus, vesicular stomatitis virus, human poliomyelitis virus, hepatitis A virus and hepatitis C virus while examples of RNA virus infecting the plants are tobacco mosaic virus, wheat dwarf virus, rice stripe virus and tobacco ringspot virus. Examples of retrovirus are adult T cell leukemia virus and human acquired immunodeficiency syndrome virus and an example of virois is potato spindle tuber viroid.

The cyclopentenone, an optically active substance thereof or a salt thereof is effective for therapy and prevention of viral diseases of non-human mammals and birds such as chicken and turkey and cold-blooded animals such as fish and such a compound has an antiviral activity to the following non-human viruses. They are sciruid herpesvirus of type 1, cavlid herpesvirus of type 1, lagomorph herpesvirus of type 1, phasianid herpesvirus of type 1, phasianid herpesvirus of type 2, turkey herpesvirus of type 1, anatid herpesvirus of type 1, catfish herpesvirus of type 1, equid herpesvirus of type 3, bovid herpesvirus of type 1, bovid herpesvirus of type 3, bovid herpesvirus of type 4, porcine herpesvirus of type 1, porcine herpesvirus of type 2, murid herpesvirus of type 1, cebid herpesvirus of type 1, cebid herpesvirus of type 2, tupalid herpesvirus of type 1, canine herpesvirus of type 1, feline herpesvirus of type 1, equid herpesvirus of type 1 and equid herpesvirus of type 2.

Viral diseases of birds such as Marek disease can be prevented and/or cured by the compound used in the present invention by the method known in veterinary or breeding such as that the antiviral agent of the present invention is injected to birds or added to feed or drinking water. Further, when the compound used in the present invention is directly added to pool, water tank, holding tank, or water, seawater, and the like in a breeding area or is mixed with the feed, the following diseases can be similarly presented and/or cured. The are viral diseases of fish living in a narrow sector such as pool, water tank, holding tank or breeding area infected with herpesvirus such as petite catfish virus, herpesvirus solomons and nerka virus and their examples are infectious necrotizing disease of hematopoietic organs, infectious diseases of herpesvirus or infectious necrotizing disease of pancreas of fish of salmon family, viral hemorrhagic septicemia of rainbow trout, spring viremia of carps, lymphocystis of various fish, viral necrotizing disease of erythrocytes of sea fish and anadromous fish, rhabdoviral disease of flatfish and the like, viral necrotizing disease of pancreas and liver of fry of yellowtail and the like, snout ulcer of torafugu (a kind of glovefish), and the like. Incidentally, the precise regulation in administering the compound used in the present invention and the antiviral agent of the present invention is naturally dependent upon the necessity for each animals to be treated, type of the treatment and judgement of the breeder.

The non-human animal to which the antiviral agent of the present invention is administered are able to maintain their health whereby the improvement in survival rate, growing rate, spawning rate, and the like is significant.

The compound having a function of inducing a resistance to virus into cells and also having a function of selectively killing the cells infected by virus such as, for example, the cyclopentenone, an optically active substance or a salt thereof used the present invention inhibits the synthesis of those viral proteins and inhibits the synthesis of virus genome as well and, accordingly, it exhibits a powerful antiviral action. In addition, it selectively kills the cells infected by those viruses.

For example, even in the patients suffering from human immunodeficiency virus (hereinafter, abbreviated as HIV), all of the CD4-positive cells are not infected by HIV but only a part of them are infected by it. The antiviral agent of the present invention inhibits the production of HIV in those infected cells, at the same time, selectively kills the infected cells, and induces the resisting ability to virus to the uninfected cells whereby it is possible to remove the HIV from the cells.

The cyclopentenone, an optically active substance or a salt thereof has an ability of improving the hepatic function and an induction activity of the heat shock protein besides the above-mentioned antiviral activity. An agent for improving the hepatic function and an agent for inducing the heat shock protein containing at least one compound selected from the cyclopentenone, an optically active substance or a salt thereof can be made into a pharmaceutical preparation by the same manner as in the case of the above--mentioned antiviral agent and can be administered by the same manner as in the case of the antiviral agent.

The dose as the agent for improving the hepatic function and for inducing the heat shock protein is not particularly specified but may be appropriately determine depending upon the dosage form, administration method, purpose of the use and age, body weight, conditions, and the like of the patient. Usually, however, the amount of at least one of the compound selected from the cyclopentenone, an optically active substance or a salt thereof contained in the preparation for an adult is 0.1 $\mu$g–20mg/kg per day. As a matter of course, the dose may vary depending upon various factors and, therefore, the dose less than the above-mentioned one may be sufficient in some cases while, in other cases, the dose more than the above may be necessary. The agent of the present invention may be administered orally as it is and, further, the agent may be taken daily after adding to common food and/or beverage as well. Further, at least on of the compound selected from the cyclopentenone, an optically active substance or a salt thereof may be used as a material for the food or beverage for improving the hepatic function or for inducing the heat shock protein.

When the cyclopentenone, an optically active substance or a salt thereof is taken, disorder in hepatic function is improved and GOT and GPT values become normal.

Moreover, the cyclopentenone, an optically active substance or a salt thereof has an induction activity of heat shock protein such as heat shock protein 70 kDa (HSP70), and the like and has an antiviral activity to RNA virus and DNA virus such as hepatitis virus, AIDS virus, influenza virus, vesicular stomatitis virus and herpesvirus. Heat shock protein participates in cancer immunity and has biodefense activity. When the cyclopentenone, an optically active substance or a salt thereof is taken, viral diseases such as cold by influenza can be prevented and cured.

Incidentally, heat shock protein is a general name for the protein whose synthesis is induced when cell or individual is subjected to a sudden temperature change which is higher than normal temperature to an extent of around 5–10° C. and it widely exists in prokaryotes and high eukaryotes. Examples of known heat shock protein are HSP90, HSP70, ubiquitin and HSP26. Among them, HSP70 is a kind of molecular chaperone and is bonded to protein where folding is not completed or is incompletely done to assist the formation of stereostructure. Amino acid sequence of the heat shock protein has been well conserved during the course of evolution and HSP70 is identical with DnaK protein of Escherichia coli. In human being, there are about ten HSP70 genes and some of them are expressed constitutionally while other are induced by various stimulations. Besides the heat shock, synthesis of heat shock protein is induced by various chemical substances and by cellular damage such as oxidation.

C. Amici, et al. reported [Journal of Virology, volume 68, pages 6890–6899 (1994)] that, when animal cells infected with Sendai virus are incubated in the presence of prostaglandin Al having α, β-unsaturated carbonyl group, synthesis of HSP70 and HSP90 is induced and that, during the synthesis of HSP70 is induced, synthesis of virus protein is inhibited. Further, A. Rossi, et al. reported [The Journal of Biological Chemistry, volume 271, pages 32192–32196 (1996)] that, like in the case of prostaglandin Al, 2-cyclopenten-1-one induces the synthesis of HSP70 and inhibits the synthesis of vesicular stomatitis virus protein.

An ability of the cyclopentenone used in the present invention for inducing HSP70 is noted at 10 $\mu$M and becomes maximum at 20–30 $\mu$M and this can be said to be a very high inducing ability as compared with the fact that a concentration of several hundred $\mu$M is required for 2-cyclopenten-1-one for inducing the HSP70. This ability is equivalent to the ability inducing the HSP70 by prostaglandin $A_1$ and, since the molecular weight of the cyclopentenone is not more than one-third of that of prostaglandin $A_1$, the cyclopentenone has a higher inducing ability than prostaglandin $A_1$ when compared in terms of concentration by weight.

Since the cyclopentenone, an optically active substance thereof or a salt thereof used in the present invention has such a high inducing ability to heat shock protein, it has antiviral activity to DNA virus, RNA virus, retrovirus and viroid. Examples of such virus and viroid are those which were mentioned hereinabove.

In addition, the cyclopentenone, an optically active substance thereof or a salt thereof has an inhibition activity of the growth of cancer cells which are transformed by cancer gene and has an activity of preventing the carcinogenesis due to cancer gene.

For example, papilloma virus is a DNA virus belonging to family Papovaviridae and genus Papillomavirus and, with respect to human papilloma virus (HPV), HPV of type 16 which is a cause of cervical cancer has been known for example.

The cyclopentenone, an optically active substance thereof or a salt thereof has an inhibition activity to the growth of cells which are cancerated by cancer gene E7 of an HPV16 type. Thus, an inhibiting agent to the growth of cancer cells which are cancerated by virus can be offered by the use of at least one compound selected from the cyclopentenone, an optically active substance thereof or a salt thereof as an effective component whereby canceration by cancer gene can be prevented.

Incidentally, the cyclopentenone, an optically active substance thereof or a salt thereof has an inhibition activity to carcinogenesis in two steps as an initiator and a promoter and it is now possible to offer an inhibiting agent to chemical canceration containing at least one compound selected from the cyclopentenone, an optically active substance thereof or a salt thereof as an effective component.

Accordingly, it is possible to offer food or beverage for prevention of carcinogenesis containing at lest one compound selected from the cyclopentenone, an optically active substance thereof or a salt thereof.

An agent for preventing the carcinogenesis by oncogene or an agent for suppressing the chemical carcinogenesis containing at least one compound selected from the cyclopentenone and an optically active substance and a salt thereof can be made into a preparation and administered by a method similar to the antiviral agent.

In the manufacture of the antiviral food or antiviral beverage of the present invention, it is possible to use a compound which has a function of inducing a resistance to virus into the cells and also a function of selectively killing the virus-infected cells such as the cyclopentenone, an optically active substance or a salt thereof. It is also possible to use a heat-treated product of uronic acid containing the cyclopentenone or a partially purified or a purified cyclopentenone obtained from said heat-treated substance.

Further, in the manufacture of action-expressing food or action-expressing beverage having an action of improving the hepatic function, inducing the heat shock proteins, preventing the carcinogenesis, and the like, it is also possible to use the cyclopentenone, an optically active substance or a salt thereof or a heat-treated product of uronic acid containing the cyclopentenone or a partially purified or a purified cyclopentenone obtained from said heat-treated substance.

Thus, food or beverage which manufactured by diluting and/or adding the cyclopentenone, an optically active substance thereof or a salt thereof, or a material selected from the cyclopentenone-containing heat treated product, partially purified cyclopentenone and purified cyclopentenone from the heat treated product is covered by the antiviral food or beverage of the present invention.

There is no particular limitation for the method of manufacturing the antiviral food or beverage of the present invention but cooking, processing and commonly-used manufacturing methods for food or beverage may be applied provided that an effective amount of at least one compound selected from the compound having a function of inducing a resistance to virus into cells and also having a function of selectively killing the cells infected by virus such as, for example, the cyclopentenone, an optically active substance or a salt thereof is contained in the resulting food or beverage.

There is no particular limitation for the shape of the antiviral food or beverage of the present invention so far as one compound selected from the compound having a function of inducing a resistance to virus into cells and also having a function of selectively killing the cells infected by virus such as, for example, the cyclopentenone, an optically active substance or a salt thereof is contained therein, added thereto and/or diluted therein. Thus, the shape includes the ones which can be orally taken such as tablets, granules, capsules, gel and sol.

There is no particular limitation for the shape of the food or beverage having an action of improving the hepatic function, inducing the heat shock proteins, preventing the carcinogenesis so far as one compound selected from the cyclopentenone, an optically active substance or a salt thereof having an action of improving the hepatic function, inducing the heat shock proteins, preventing the carcinogenesis is contained therein, added thereto and/or diluted therein. Thus, the shape includes the ones which can be orally taken such as tablets, granules, capsules, gel and sol.

The food or beverage of the present invention contains the cyclopentenone, an optically active substance or a salt thereof having the physiological activities and, due to various physiological activities of said compound such as antiviral activity, activity of improving the hepatic function, inducing the heat shock proteins, preventing the carcinogenesis, and the like, it is a healthy food or beverage having viral diseases-preventing and -treating effects, hepatic function improving effect, carcinogenesis-preventing effect, and the like and, further it is food or beverage which is useful for maintaining the homeostasis of living body.

No toxicity was observed in the compound used in the present invention even when the dose which is effective to achieve those physiological activities is administered. In the case of oral administration for example, no dead case was observed in rats by a single oral administration of 100 mg/kg of any of the cyclopentenone, an optically active substance or a salt thereof.

To sum up, the pharmaceutical agent of the present invention can be used as a therapeutic or a preventive agent for viral diseases, hepatic diseases, cancer, and the like and is particularly useful for the therapy of AIDS induced by HIV and for improvement of said syndrome.

EXAMPLES

The present invention will be further illustrated by way of the following examples although the present invention is never limited to those examples. Incidentally, "%" used in the examples stands for "% by weight".

REFERENTIAL EXAMPLE 1

D-Glucuronic acid (G 5269; manufactured by Sigma) (10 g) was dissolved in 1 liter of water, heated at 121° C. for four hours and concentrated in vacuo until about 10 ml. This was mixed with 40 ml of an upper layer of a 3:2:2 mixture of butyl acetate, acetic acid and water and centrifuged and the resulting supernatant liquid was concentrated in vacuo until about 10 ml.

The above extract was applied to silica gel (BW-300SP; 2×28 cm; manufactured by Fuji Silycia) for a column chromatography and separated using an upper layer of a 3:2:2 mixture of butyl acetate, acetic acid and water as an eluate at the flow rate of about 5 ml/minute under a pressure of 0.2 kg/cm2 using a compressor. Fractionation was conducted to make a volume of one fraction 10 ml and a part of each fraction was analyzed by a thin layer chromatography whereupon cyclopentenone of a high purity was contained in 61st to 80th fractions. Those fractions were collected, concentrated in vacuo, extracted with 40 ml of chloroform and the extract was concentrated in vacuo to afford 100 mg of cyclopentenone.

The fraction was separated by means of a normal phase HPLC using a Palpack type S column (manufactured by Takara Shuzo) and, when a detection was conducted by an ultraviolet absorption of 215 nm, the purity was found to be 98%.

The above cyclopentenone (113.9 mg) was dissolved in 2.85 ml of ethanol. To this ethanolic solution was added 3.85 ml of hexane/ethanol (94/6) to prepare a cyclopentenone solution (17 mg/ml). This solution was filtered through a filter of 0.5 µm to prepare a sample solution for an optical resolution HPLC.

This sample solution was applied to an optical resolution HPLC, each of the fractions of the (−)-cyclopentenone in the earlier peak and the (+)-cyclopentenone in the later peak was collected and evaporated to dryness in vacuo to give 43.2 mg of the (−)-cyclopentenone and 43.0 mg of the (+)-cyclopentenone.

Conditions for Optical Resolution HPLC.

Columns: Chiral Pack AS (manufactured by Daicel) 2.0 cm×25.0 cm

Column temperature: 40° C.

Mobile phase: hexane/ethanol (94/6)

Flow rate: 14.0 ml/minute

Detection: UV 210 nm

Amount of the charged sample: 150 µl (2.55 mg)

Each of the (−)-cyclopentenone and (+)-cyclopentenone obtained herein contains about 1% of enantiomer and, therefore, they were subjected to an optical resolution under the above-mentioned conditions again. As a result, 19.7 mg of the (−)-cyclopentenone containing no enantiomer was obtained from 30.0 mg of the (−)-cyclopentenone of the earlier peak while, from 37.4 mg of the (+)-cyclopentenone of the later peak, 27.7 mg of the (+)-cyclopentenone containing no enantiomer was obtained. Incidentally, the eluting times in optical resolution HPLC of the (−)-cyclopentenone and (+)-cyclopentenone were 33 minutes and 40 minutes, respectively.

Example 1

(1) An RPMI 1640 medium (5 ml) containing 10% of fetal bovine serum which contained $2 \times 10^5$ cells/ml of human promyelocytic leukemia cells HL-60 (ATCC CCL-240) was placed in each well of a six-well plate, incubated at 37° C. for 24 hours in the presence of 5% of $CO_2$, then the cyclopentenone described in the referential example L was added thereto to make its final concentration 0, 10, 20, 30, 40, 50, or 100 µM and the incubation was further continued for eight hours more.

After completion of the incubation, cell numbers were counted and the cells were recovered by centrifugation and washed with phosphate-buffered saline (PBS) to prepare cyclopentenone-treated cells. In the meanwhile, cells which were heated at 45° C. for ten minutes followed by subjecting to the same incubation were prepared as well.

The cells treated as such were subjected to an SDS-polyacrylamid gel electrophoresis (SDS-PAGE) by a method mentioned in "Molecular Cloning" [Cold Spring Harbor Laboratory Press, (1989)]. The treated cells were suspended in an SDS-PAGE sample buffer to make the concentration $2.5 \times 10^6$ cells/ml, the resulting cell suspension was treated at 100° C. for ten minutes and each 5 µl thereof was applied to two sheets of SDS-PAGE gels (5% stacking gel; 10% separation gel) to conduct anelectrophoresis. One of the gels was Coomassie stained while another gel was subjected to a blotting to a polyvinylidene difluoride transfer membrane (Immobilon™, manufactured by Millipore, catalog no. IPVH000-10). The membrane was subjected to a blocking at 4° C. for one night with Block Ace (manufactured by Dainippon Pharmaceutical; catalog no. UK-B25).

The blocked membrane was made to react with monoclonal antibody HSP 72/73 (Ab-1) (manufactured by Oncogene Research Products, catalog no. HSP01) which would specifically react with heat-induced heat shock protein of 70 kDa and washed with TBS containing 0.05% of Tween 20 followed by further washing with TBS. After that, it was made to react with peroxidase-compounded secondary antibody HRP-Rabbit Anti-Mouse IgG (H+L) (manufactured by Zymed Laboratories, catalog no. 61-6520) and washed by the same manner as in the above operation. The membranes which were treated with primary and secondary antibodies as such were made to react with Renaissance™ (a chemiluminor reagent manufactured by Dupont NEN, catalog no. NEL-100) and photosensitized with an X-ray film to confirm the induction of heat shock protein of 70 kDa.

The result was that, by addition of cyclopentenone (20 to 30 µM), induction of heat shock protein of 70 kDa which is almost same as heat-treated at 45° C. for 10 minutes was confirmed. Intensity of the induction is shown in Table 1. In Table 1, "+" indicates degree of intensity of induction and the more the numbers of "+", the more the intensity of induction. Incidentally, "−" means that no induction was noted and "±" means the induction was slight.

TABLE 1

| Treated Cells | Induction of Heat Shock Proteins |
|---|---|
| Heated at 45° C. for 10 minutes | +++ |
| 0 μM of the cyclopentenone | - |
| 10 μM of the cyclopentenone | + |
| 20 μM of the cyclopentenone | +++ |
| 30 μM of the cyclopentenone | +++ |
| 40 μM of the cyclopentenone | ++ |
| 50 μM of the cyclopentenone | + |
| 100 μM of the cyclopentenone | ± |

Same results were obtained in the case of the (−)-cyclopentenone and the (+)-cyclopentenone as well.

Example 2

(1) HeLa cells (ATCC CCL-2) were incubated in a Dulbecco-modified Eagle's medium (DMEM; manufactured by Nissuisha) containing 10% fetal bovine serum in a 10 cm plate at 37° C. in the presence of 5% carbon dioxide gas until a 80% confluence was resulted, then the cyclopentenone was added thereto so that its final concentration was made 0, 5, 10, 20 or 40 μM and incubation was continued for additional six hours under the above-mentioned conditions. The medium was discarded, 1 ml of 10% trichloroacetic acid was added to each of the wells and the cells were recovered by a scraper.

The cells prepared as such were subjected to an SDS-PAGE and a blotting according to a method of Example 1 to detect the expression of 70 kd heat shock proteins.

As a result, induction of the 70 kd heat shock proteins noted in the sections to which the cyclopentenone of from 5 μM to 40 μM was added. The result is given in Table 2. Incidentally, in Table 2, the sign "+" shows the potency of signals of the 70 kd heat shock proteins observed in the blotting the more the numbers of +, the more potent the signals. The sign "±" means that the signal was very weak.

TABLE 2

| Treated Cells | Amount of 70 kd of Heat Shock Proteins |
|---|---|
| 0 μM of the cyclopentenone | ± |
| 5 μM of the cyclopentenone | + |
| 10 μM of the cyclopentenone | ++ |
| 20 μM of the cyclopentenone | +++ |
| 40 μM of the cyclopentenone | +++ |

(2) HeLa cells were incubated in a DMEM containing 10% fetal bovine serum in a 10 cm plate at 37° C. in the presence of 5% carbon dioxide gas until a 80% confluence was resulted, then the cyclopentenone was added thereto so that its final concentration was made 0, 5, 10, 20 or 40 μM and incubation was continued for additional six hours under the above-mentioned conditions. After that, the cells were washed with the DMEM containing 5% of fetal bovine serum, then the DMEM containing 5% of fetal bovine serum which contained Ad5 dlX [an adenovirus; Saito, etal.; Journal ofVirology, volume 54, pages 711–719 (1985)] was added to the cells so that the cells were infected therewith and incubation was conducted for 20 hours. Incidentally, the multiplicity. of infections (m.o.i.) was adjusted to 50. The medium was discarded, 1 ml of 10% trichloroacetic acid was added to each of the wells and the cells were recovered by a scraper.

Then SDS-PAGE and blotting of the treated cells obtained hereinabove were conducted by the method of Example 1 to detect the expression of hexon proteins of the adenovirus. Incidentally, anti-adenovirus hexon antibody (AB 1056; manufactured by Chemicon International Inc.) was used as the primary antibody.

In the section to which 10 μM or higher cyclopentenone was added, the amount of the hexon protein apparently decreased as compared with the control to which none of the cyclopentenone was added. In the sections to which 20 μM or lower amount of the cyclopentenone was added, growth of the cells similar to that in the section to which none of the cyclopentenone was added was observed.

(3) Viral DNA was extracted according to a method mentioned in "Protocols for Experiments of Virus" (pages 24–25; published by Medical View) from the HeLa cells which were treated with the cyclopentenone and infected by adenovirus followed by incubation by the same manner as in Example 2-(2).

Thus, cells infected by virus were washed with a saline solution buffered by phosphoric acid, suspended in 1 ml of aqueous solution of 0.6% sodium laurylsulfate (SDS) and 10 mM EDTA and 3.0 ml of 5M aqueous solution of sodium chloride was added thereto. The mixture was allowed to stand at 0° C. for one hour and centrifuged and 3 ml of ethanol was added to the resulting supernatant liquid followed by mixing. The precipitate obtained by centrifugal separation was dissolved in 0.2 ml of TE buffer (10 mM Tris-HCl of pH 8.0 and 1 mM EDTA), then 2 μl of 10% SDS and 4 μl of 10 mg/ml proteinase K (manufactured by Takara Shuzo) were added thereto and the mixture was kept at 37° C. for one hours. This was extracted with a mixture of equal amounts of phenol and chloroform twice, 20 μl of 3M sodium acetate and 400 μl of ethanol were added to the aqueous layer, the mixture was centrifuged and the precipitate was dissolved in 50 μl of the TE buffer to give a DNA solution. The DNA solution (10 μl) was digested with 10 units of EcoT22I (manufactured by Takara Shuzo) and 1 μl of 10 mg/ml ribonuclease A and then subjected to an agarose gel electrophoresis to determine the amount of viral DNA. The result was that there was an apparent decrease in the amount of viral DNA in the sections to which 5 μM or more of the cyclopentenone was added as compared with the control where none of the cyclopentenone was added.

(4) After HeLa cells were incubated by the same manner as in Example 2-(2), DMEM containing 5% of fetal bovine serum which contained adenovirus of type 5 (Adenoid 75; ATCC VR-5) was added to the cells without addition of the cyclopentenone whereby the cells were infected by that. Incidentally, multiplicity of infections (m.o.i.) was adjusted to 50. After that, the cyclopentenone was added thereto to make its final concentration 0, 5, 10, 20 or 40μM and incubationwas conducted for 20 hours. After the incubation, detection of hexon proteins of adenovirus was conducted by the same manner as in Example 2-(2). The result was that there was an apparent decrease in the amount of hexon proteins in the sections to which 10 μM or more of the cyclopentenone was added as compared with the control to which none of the cyclopentenone was added. Incidentally, growth of the cells were in the sections to which 20 μM or more of the cyclcopentenone was added was as same as that in the sections to which none of the cyclopentenone was added.

(5) HeLa cells were incubated by the same manner as in Example 2-(2) and treated with the cyclopentenone. After that, the cells were infected by the adenovirus type 5 (Adenoid 75; ATCC VR-5) by the same manner as in Example 2-(4) and incubated in a medium to which the cyclopentenone was added. After the incubation, detection of the hexon proteins of adenovirus was conducted by the same manner as in Example 2-(2). The result was that there was an apparent decrease in the amount of the hexon proteins in the sections to which 10 μM or more of the cyclopentenone was added as compared with the control to which none of the cyclopentenone was added. Incidentally, growth of the cells was noted in the sections to which 20 μM or less of the cyclopentenone was added as same as in the section to which none of the cyclopentenone was added.

(6) Amount of the viral DNA was measured by the same manner as in Example 2-(3) from the HeLa cells which were treated with the cyclopentenone infected by the adenovirus type 5 (Adenoid 75; ATCC VR-5) followed by incubating by the same manner as in Example 2-(5). The result was that there was an apparent decrease in the amount of the viral DNA in the sections to which 5 μM or more of the cyclopentenone was added as compared with the control to which none of the cyclopentenone was added.

From the results of the above-mentioned Examples 2-(2) ~(6), it was apparent that administration of the cyclopentenone before, after or before and after the infection exhibited antiviral activity to adenovirus. Same results were obtained in the case of the (−)-cyclopentenone and the (+)-cyclopentenone as well.

Example 3

(1) Recombined retrovirus vector BAG having β-galactosidase gene and neomycin-resistant gene as reporter genes as mentioned in Proceedings of the National Academy of Sciences of the U. S. A., volume 84, pages 156–160 (1987) was digested by a restriction enzyme BamHI to conduct a self-ligation whereupon DOL wherefrom β-galactosidase gene was eliminated was constructed.

(2) DOL vector plasmid mentioned in Example 3-(1) was transformed to E. coli HB 101, incubated in an L-broth medium, plasmid was extracted from the collected cells and the DOL plasmid was purified by means of a cesium chloride density-gradient ultracentrifugation.

The purified DOL plasmid (10 μg) was introduced into retrovirus packaging cell Ψ CRIP [Proceedings of the National Academy of Sciences of the U. S. A., volume 85, pages 6460–6464 (1988)] using a cationic liposome (Trans 2T LT-1; manufactured by Takara Shuzo).

The cells after the introduction were selected for two weeks at 37° C. under the condition of 5% $CO_2$ in a 10% calf serum-containing Dulbecco-modified Eagle's medium containing 0.4 mg/ml of G418 (Gibco), 20 colonies selected thereby were cloned and promulgated in a plate having a diameter of 100 mm, the medium was exchanged under the semiconfluent condition, the supernatant liquid was recovered after 24 hours and filtered through a filer of 0.45 μm (Milex HV; manufactured by Millipore) to give a supernatant liquid of the virus. In the mean while, the cells were scraped off with trypsin and preserved in liquid nitrogen.

Titer of the supernatant liquid of the virus obtained from each of the colonies was determined by the method mentioned in the following Example 3-(3) and the clone wherefrom the virus solution of the highest titer was obtained was established as a recombinant retrovirus producer cell Ψ CRIP/DOL. The titer of the supernatant liquid of the virus obtained from the producer cells at the time of the establishment was $1\times10^6$ colony forming units (cfu) /ml. The producer cells established as such were maintained in a 10% calf serum-containing Dulbecco-modified Eagle's medium containing 0.2 mg/ml of G418.

(3) NIH3T3 cells (ATCC CRL-1658) were used for the measurement of the titer of the virus. The NIH3T3 cells incubated in a Dulbecco-modified Eagle's medium containing 10% calf serum were transplanted at the rate of 50,000 cells/well of a six-well plate (Iwaki Glass) and, on the next day, they were infected to NIH3T3 cells for three hours using 1 ml of diluted virus solution containing 8 μg/ml of Polybrene (Sigma). For diluting the virus, a Dulbecco-modified Eagle's medium containing 10% of calf serum was used. After completion of the infection, more 2 ml of a Dulbecco-modified Eagle's medium containing 10% of calf serum was added for diluting the Polybrene. As from the next day, exchange with a 10% calf serum-containing Dulbecco-inodified Eagle's medium containing 0.4 mg/ml of G418 was conducted. Selection was conducted for two weeks by exchanging the medium as above every three to four days whereupon colonies were formed. The resulting colonies were stained by a conventional manner using a Giemsa staining liquid (Gibco) to count. The value obtained by multiplying the counted colony numbers by degree of the dilution was defined as cfu and used as the titer of the virus.

(4) The recombinant retrovirus producer cells Ψ CRIP/DOL mentioned in Example 3-(2) were transplanted to a six-well plate and, when the semiconfluent state was resulted, exchanging with 1.5 ml of a 10% calf serum-containing Dulbecco-modified Eagle's medium containing 0~20 μM of the cyclopentenone was conducted. After 24 hours, the supernatant liquid was recovered. Titer of the virus in the recovered supernatant liquid were measured by the method mentioned in Example 2-(3) and the influence of the recombinant retrovirus producer cells on the productivity of virus by addition of the cyclopentenone was investigated.

The titer of the virus solution obtained from the control experimental section to which none of the cyclopentenone was added was $9.5\times10^4$ cfu/ml while those of the virus solutions in the presence of 0.1, 0.5, 1.0, 2.0, 5.0, 10 and 20 μM of the cyclopentenone were $8.3\times10^4$, $6.4\times10^4$, $6.1\times10^4$, $3.8\times10^4$, $5.6\times10^4$, $5.1\times10^4$ and $4.1\times10^4$ cfu/ml, respectively whereupon it was ascertained that the titer of virus solutions obtained from the producer cells decreases by addition of the cyclopentenone. Thus, the an action of the cyclopentenone for suppressing the virus productivity of the recombinant retrovirus producer cells was confirmed.

(5) Control plasmid pcD2-Y expressing the G418-resistant genes [Mol. Cell. Biol., volume 7, pages 2745–2752 (1987)] and plasmid pcD2-16E7 expressing both HPV16-type E7 and G418-resistant genes [Jpn. J. Cancer Res., volume 82, pages 1340–1343 (1881)] were transformed to E. coli HB 101, incubated in an L-broth medium and the plasmid was extracted from the collected cells and purified by means of a cesium chloride density-gradient ultracentrifugation to give vector plasmid for introduction of genes.

NIH3T3 cells were incubated in a Dulbecco-modified Eagle's medium containing 10% of calf serum at 37° C. under the condition of 5% of $CO_2$.

The purified plasmid (10 μg) was introduced into the NIH3T3 cells using a cationic liposome (TransIT LT-1; manufactured by Takara Shuzo), the cells were selected for two weeks in a 10% calf serum-containing Dulbecco-modified Eagle's medium containing 0.4 mg/ml of G418 (Gibco) under the condition of 5% of $CO_2$ and the resulting colonies were cloned, cultivated in a tissue culture plate of a 100 mm diameter and preserved in liquid nitrogen successively.

As a result thereof, each nine strains of NIH 3T3 cells into which control vectors were introduced and NIH 3T3 cells which were tumorgenically transformed by HPV 16 type E7 were established.

The cell strains irto which the control vectors were introduced were named NIH3T3/Y-1, NIH3T3/Y-2, NIH3T3/Y-3, NIH3T3/Y-4, NIH3T3/Y-5, NIH3T3/Y-6, NIH3T3/Y-7, NIH3T3/Y-8 and NIH3T3/Y-9.

The cell strains into which E7 was introduced were named NIH3T3/E7-1, NIH3T3/E7-2, NIH3T3/E7-3, NIH3T3/E7-4, NIH3T3/E7-5, NIH3T3/E7-6, NIH3T3/E7-7, NIH3T3/E7-8, and NIH3T3/E7-9.

(6) NIH3T3 cells, the cell strains into which the control vectors were introduced and the cell strains into which E7 was introduced were cultivated to an extent of 50–70% confluence in a 100-mm tissue culture plate using a Dulbecco-modified Eagle's medium containing 1.0% of calf serum and washed with PBS and the cells were scraped off with 0.25% trypsin-EDTA solution and suspended in 5 ml of a Dulbecco-modified Eagle's medium containing 10% of calf serum.

A part of the suspension was taken out and cell density thereof was calculated using a blood counter of a Newbauer type. Based upon the resulting data, the suspension was diluted with a Dulbecco-modified Eagle's medium containing 10% of calf serum and sowed on a tissue culture plate having a diameter of 60 mm to make the concentration 200 cells/plate and incubation was started in 3 ml of the medium. After 24 hours from the initiation of the incubation, the cyclopentenone was added thereto to an extent of 5 $\mu$M. After more 24 hours, the medium was exchanged with a fresh one and the cyclopentenone was added to an extent of 5 $\mu$M.

After that, the medium was exchanged and the cyclopentenone was added to an extent of 5 $\mu$M every two to three days. As a control experimental section, a plate to which none of the cyclopentenone was added was prepared and the medium was exchanged in the same manner as above. Each incubation was conducted in three runs. After incubating for nine days, fixation with methanol was conducted and the colonies were stained with a Giemsa solution (Gibco).

Incidentally, evaluation was conducted using NIH3T3, NIH3T3/Y-1 and NIH3T3/E7-2.

Results of counting the stained colonies are given in Table 3. The cells into which E7 was introduced showed high sensitivity to the cyclopentenone as compared with the control cells. Thus, the cyclopentenone selectively acted to the cells transformed by oncogenes.

TABLE 3

| Cells Used | Numbers (average ± SD) of the Colonies | |
|---|---|---|
| | Control | Cyclopentenone-Treated Cells |
| NIH3T3 | 91.7 ± 11.9 | 85.3 ± 4.0 |
| NIH3T3/Y-1 | 83.3 ± 8.4 | 71.3 ± 2.3 |
| NIH3T3/E7-2 | 67.3 ± 3.2 | 22.3 ± 3.5 |

Similar results were obtained when other cell strains of Example 3-(5) were used. In addition, the (−)-cyclopentenone and the (+)-cyclopentenone gave the similar results as well.

Example 4

(1) To the MDCK cells (preserved at the Prefectural Public Hygiene Laboratory, Osaka Prefecture) incubated in a 24-well microplate using an Eagle's MEM containing 10% fetal bovine serum in the presence of 5% carbon dioxide gas until monolayers were obtained was added the cyclopentenone to make its final concentration 0, 5, 10, 20 or 40 $\mu$M and the incubation was continued for six hours more under the above-mentioned conditions.

After that, the cells were washed with PBS, infected by influenza virus A/PR/8/34 strain (preserved at the Prefectural Public Hygiene Laboratory, Osaka Prefecture) and incubated at 37° C. for 30 minutes. Incidentally, the multiplicity of infections (m.o.i.) was adjusted to 0.01. After incubation, the cells were washed with PBS and incubated in an Eagle's MEM containing 10 $\mu$g/ml of trypsin.

The supernatant liquid of the infected cells was collected on 0, 1, 2 and 3 day(s) thereafter and the titer of the virus was determined by a PAP method using a focus counting method [J. Clin. Microbiol., volume 28, pages 1308–1313 (1990)].

The result was that,, in the sections to which 10 $\mu$M or more of the cyclopentenone was added, the titer of the virus apparently lowered as compared with the control to which none of the cyclopentenone was added. The result is given in Table 4. In addition, the cells were not eliminated but adhered in each of the sections to which the cyclopentenone was added.

TABLE 4

| Days after Infection | Concentration of the Cyclopentenone ($\mu$M) | | | | |
|---|---|---|---|---|---|
| | 0 pfu/ml | 5 pfu/ml | 10 pfu/ml | 20 pfu/ml | 40 pfu/ml |
| 0 | <1.0 × 10$^2$ | <1.0 × 10$^2$ | <1.0 × 10$^2$ | <1.0 × 10$^2$ | <1.0 × 10$^2$ |
| 1 | 3.6 × 10$^5$ | 4.0 × 10$^5$ | 2.0 × 10$^5$ | 2.2 × 10$^3$ | 4.0 × 10$^2$ |
| 2 | 1.0 × 10$^6$ | 8.0 × 10$^5$ | 7.2 × 10$^5$ | 2.6 × 10$^5$ | 1.9 × 10$^5$ |
| 3 | 1.5 × 10$^5$ | 9.6 × 10$^4$ | 2.4 × 10$^5$ | 3.8 × 10$^5$ | 5.6 × 10$^5$ |

(2) According to the same operations as in Example 4-(1), influenza virus was added to the MDCK cells incubated to monolayers in the absence of the cyclopentenone and said cells were infected by said virus by the same manner as in Example 4-1) and incubated in an Eagle's MEM containing 10 $\mu$g/ml of trypsin to which the cyclopentenone was added to make its final centration 0, 5, 10, 20 or 40 $\mu$M. After that, the titer of the virus was determined by the same manner as in Example 4-1). The result was that, in the sections to which 10 $\mu$M or more of the cyclopentenone was added, the titer of the virus apparently lowered as compared with the control to which none of the cyclopentenone was added. The result is given in Table 5. In addition, the cells were not eliminated but adhered in each of the sections to which the cyclopentenone was added.

TABLE 5

| Days after Infection | Concentration of the Cyclopentenone ($\mu$M) | | | | |
|---|---|---|---|---|---|
| | 0 pfu/ml | 5 pfu/ml | 10 pfu/ml | 20 pfu/ml | 40 pfu/ml |
| 0 | <1.0 × 10$^2$ | <1.0 × 10$^2$ | <1.0 × 10$^2$ | <1.0 × 10$^2$ | <1.0 × 10$^2$ |
| 1 | 4.2 × 10$^6$ | 2.4 × 10$^5$ | 1.9 × 10$^5$ | 1.2 × 10$^5$ | <1.0 × 10$^2$ |
| 2 | 1.6 × 10$^6$ | 1.5 × 10$^6$ | 3.4 × 10$^5$ | 1.0 × 10$^6$ | <1.0 × 10$^2$ |
| 3 | 4.8 × 10$^5$ | 1.9 × 10$^5$ | 1.7 × 10$^5$ | 7.2 × 10$^5$ | <1.0 × 10$^2$ |

(3) According to the same operations as in Example 4-(1), MDCK cells which were incubated to monolayers and treated with the cyclopentenone of the final concentration of 0, 20 or 40 μM for six hours and were infected by influenza virus by the same manner as in Example 4-(1) and incubation was continued in an Eagle's MEM containing 10 μg/ml of trypsin in which the cyclopentenone of the same concentration as same as before the infection. After that, the titer of the virus was determined by the same manner as in Example 4-(1). The result was that, in the sections to which 20 μM or more of the cyclopentenone was added, the titer of the virus apparently lowered as compared with the control to which none of the cyclopentenone was added. The result is given in Table 6. In addition, the cells were not eliminated but adhered in each of the sections to which the cyclopentenone was added.

TABLE 6

| Days after Infection | Concentration of the Cyclopentenone (μM) | | |
|---|---|---|---|
| | 0 pfu/ml | 20 pfu/ml | 40 pfu/ml |
| 0 | $<1.0 \times 10^2$ | $<1.0 \times 10^2$ | $<1.0 \times 10^2$ |
| 1 | $4.6 \times 10^5$ | $9.8 \times 10^4$ | $<1.0 \times 10^2$ |
| 2 | $6.6 \times 10^5$ | $1.6 \times 10^5$ | $<1.0 \times 10^2$ |
| 3 | $1.0 \times 10^5$ | $1.3 \times 10^5$ | $<1.0 \times 10^2$ |

(4) The same experiment as in Example 4-(1) was conducted where the multiplicity of infections (m.o.i.) was adjusted to 0.001. The result was that, in the sections to which 10 μM or more of the cyclopentenone was added, the titer of the virus apparently lowered as compared with the control to which none of the cyclopentenone was added. The result is given in Table 7. In addition, the cells were not eliminated but adhered in each of the sections to which the cyclopentenone was added.

TABLE 7

| Days after Infection | Concentration of the Cyclopentenone (μM) | | | | |
|---|---|---|---|---|---|
| | 0 pfu/ml | 5 pfu/ml | 10 pfu/ml | 20 pfu/ml | 40 pfu/ml |
| 0 | $<1.0 \times 10^2$ | $<1.0 \times 10^2$ | $<1.0 \times 10^2$ | $<1.0 \times 10^2$ | $<1.0 \times 10^2$ |
| 1 | $<1.0 \times 10^2$ | $<1.0 \times 10^2$ | $<1.0 \times 10^2$ | $<1.0 \times 10^2$ | $<1.0 \times 10^2$ |
| 2 | $3.6 \times 10^5$ | $5.2 \times 10^5$ | $6.2 \times 10^5$ | $5.0 \times 10^5$ | $4.4 \times 10^3$ |
| 3 | $3.8 \times 10^4$ | $4.0 \times 10^4$ | $8.6 \times 10^4$ | $1.1 \times 10^5$ | $8.0 \times 10^3$ |

(5) The same experiment as in Example 4-(2) was conducted where the multiplicity of infections (m.o.i.) was adjusted to 0.001. The result was that, in the sections to which 10 μM or more of the cyclopentenone was added, the titer of the virus apparently lowered as compared with the control to which none of the cyclopentenone was added. The result is given in Table 8. In addition, the cells were not eliminated but adhered in each of the sections to which the cyclopentenone was added.

TABLE 8

| Days after Infection | Concentration of the Cyclopentenone (μM) | | | | |
|---|---|---|---|---|---|
| | 0 pfu/ml | 5 pfu/ml | 10 pfu/ml | 20 pfu/ml | 40 pfu/ml |
| 0 | $<1.0 \times 10^2$ | $<1.0 \times 10^2$ | $<1.0 \times 10^2$ | $<1.0 \times 10^2$ | $<1.0 \times 10^2$ |
| 1 | $6.0 \times 10^2$ | $<1.0 \times 10^2$ | $<1.0 \times 10^2$ | $<1.0 \times 10^2$ | $<1.0 \times 10^2$ |
| 2 | $3.6 \times 10^5$ | $8.8 \times 10^4$ | $2.0 \times 10^5$ | $1.8 \times 10^4$ | $<1.0 \times 10^2$ |
| 3 | $3.8 \times 10^4$ | $2.6 \times 10^4$ | $1.8 \times 10^4$ | $1.2 \times 10^4$ | $<1.0 \times 10^2$ |

(6) The same experiment as in Example 4-(3) was conducted where the multiplicity of infections (m.o.i.) was adjusted to 001. The result was that, in the sections to which 10 μM or more of the cyclopentenone was added, the titer of the virus apparently lowered as compared with the control to which none of the cyclopentenone was added. The result is given in Table 9. In addition, the cells were not eliminated but adhered in each of the sections to which the cyclopentenone was added.

TABLE 9

| Days after Infection | Concentration of the Cyclopentenone (μM) | | | | |
|---|---|---|---|---|---|
| | 0 pfu/ml | 5 pfu/ml | 10 pfu/ml | 20 pfu/ml | 40 pfu/ml |
| 0 | $<1.0 \times 10^2$ | $<1.0 \times 10^2$ | $<1.0 \times 10^2$ | $<1.0 \times 10^2$ | $<1.0 \times 10^2$ |
| 1 | $6.0 \times 10^3$ | $<1.0 \times 10^2$ | $<1.0 \times 10^2$ | $<1.0 \times 10^2$ | $<1.0 \times 10^2$ |
| 2 | $6.2 \times 10^5$ | $4.4 \times 10^5$ | $4.8 \times 10^5$ | $3.2 \times 10^4$ | $<1.0 \times 10^2$ |
| 3 | $3.6 \times 10^4$ | $5.6 \times 10^4$ | $2.8 \times 10^4$ | $2.8 \times 10^4$ | $<1.0 \times 10^2$ |

From the results of the above-mentioned Examples 4-)~(6), it was apparent that the cyclopentenone exhibited antiviral activity to influenza virus. In addition, the (−)-cyclopentenone and the (+)-cyclopentenone gave the similar results as well.

Example 5

(1) Action of the Cyclopentenone to Human T Cells.

The cyclopentenone (0.5-5 m M) was added to $2 \times 10^5$ cells/ml of the CEM-SS cells (ATCC CCL-119) or to H9 cells (ATCC B-176) and incubated for three days and the numbers of living cells and of dead cells were counted whereupon the survival rates of the cells were calculated.

Figure 2:
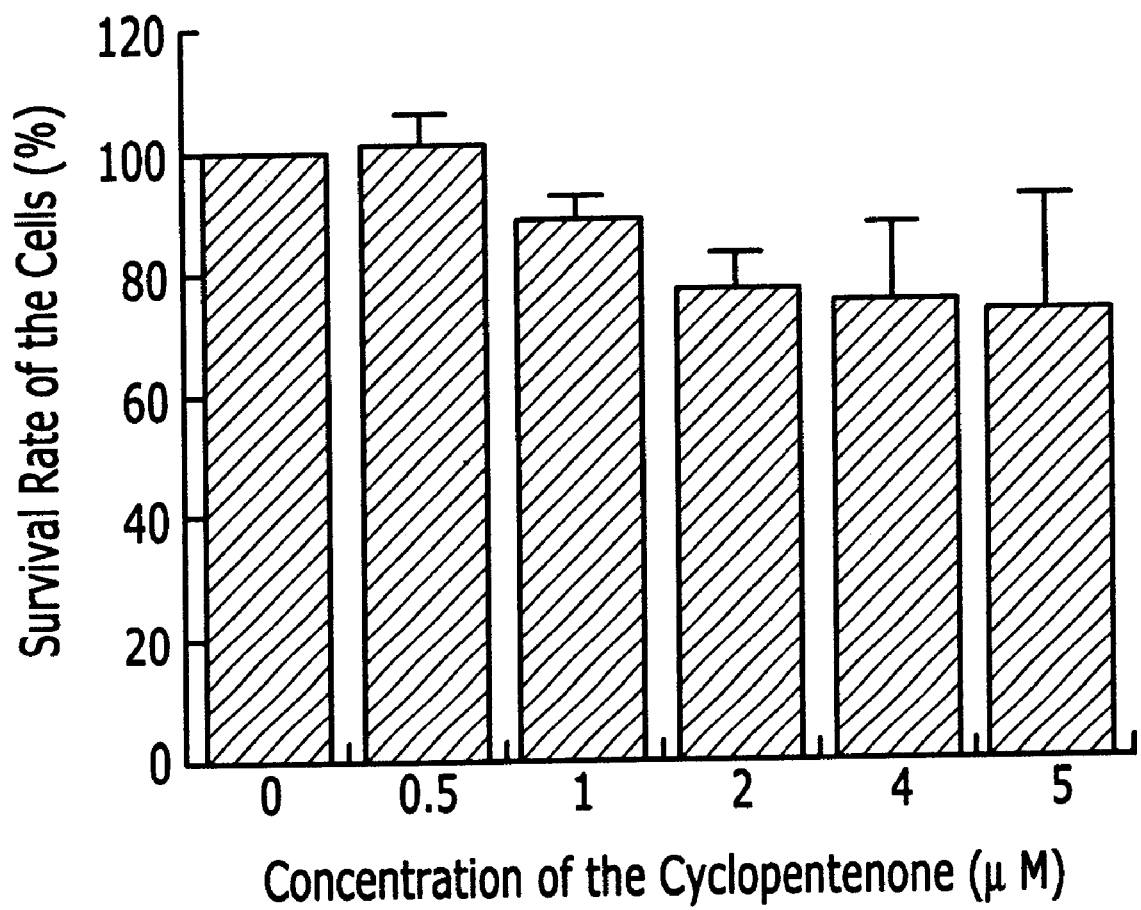
FIG. 2 is a graph showing the relation between the concentration of the cyclopentenone and the survival rate when H9 cells are used.

The result was that, in both cells, there was no significant decrease in the survival rate of the cells by addition of the cyclopentenone. The result is given in FIG. 1 and in FIG. 2. Thus, FIG. 1 and FIG. 2 are the graphs showing the relation between the concentration of the cyclopentenone added and the survival rate of the cells in which abscissa is the concentration (μM) of the cyclopentenone added while ordinate is the survival rate (%) of the cells after incubating for three days. FIG. 1 is a result when CEM-SS cells were used while FIG. 2 is a result when H9 cells were used.

(2) Action of the Cyclopentenone to HIV-InfectedT Cells.

The cyclopentenone (1-5 μM) was added to CEM-SS cells infected by HIV-1$_{IIIB}$ (abbreviated as CEM-3B) or to H9 cells infected by HIV-1$_{IIIB}$ (abbreviated as H9-3B) and incubated for three days. In both cells, 90% or more of the cells were infected by HIV-1$_{IIIB}$. Numbers of living and dead cells were counted and the survival rate of the cells was calculated therefrom.

Figure 3:
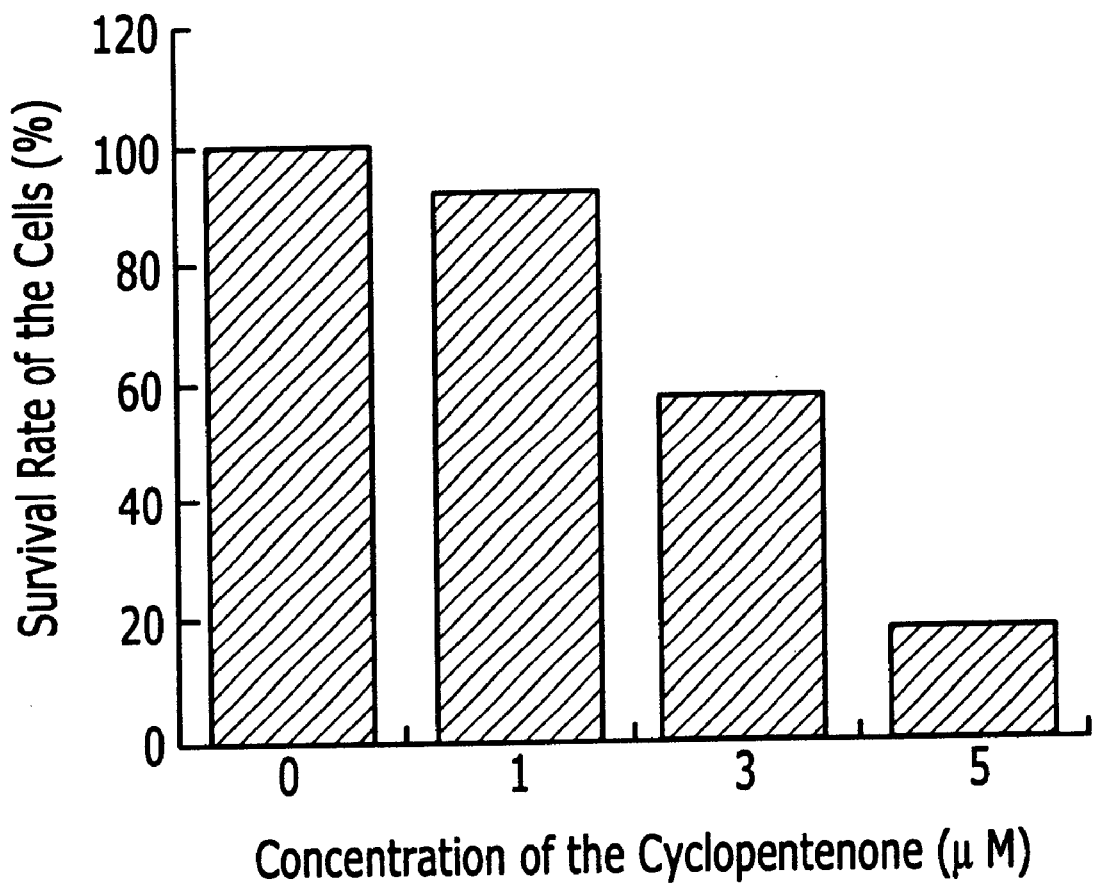
FIG. 3 is a graph showing the relation between the concentration of the cyclopentenone and the survival rate when CEM-3B cells are used.
Figure 4:
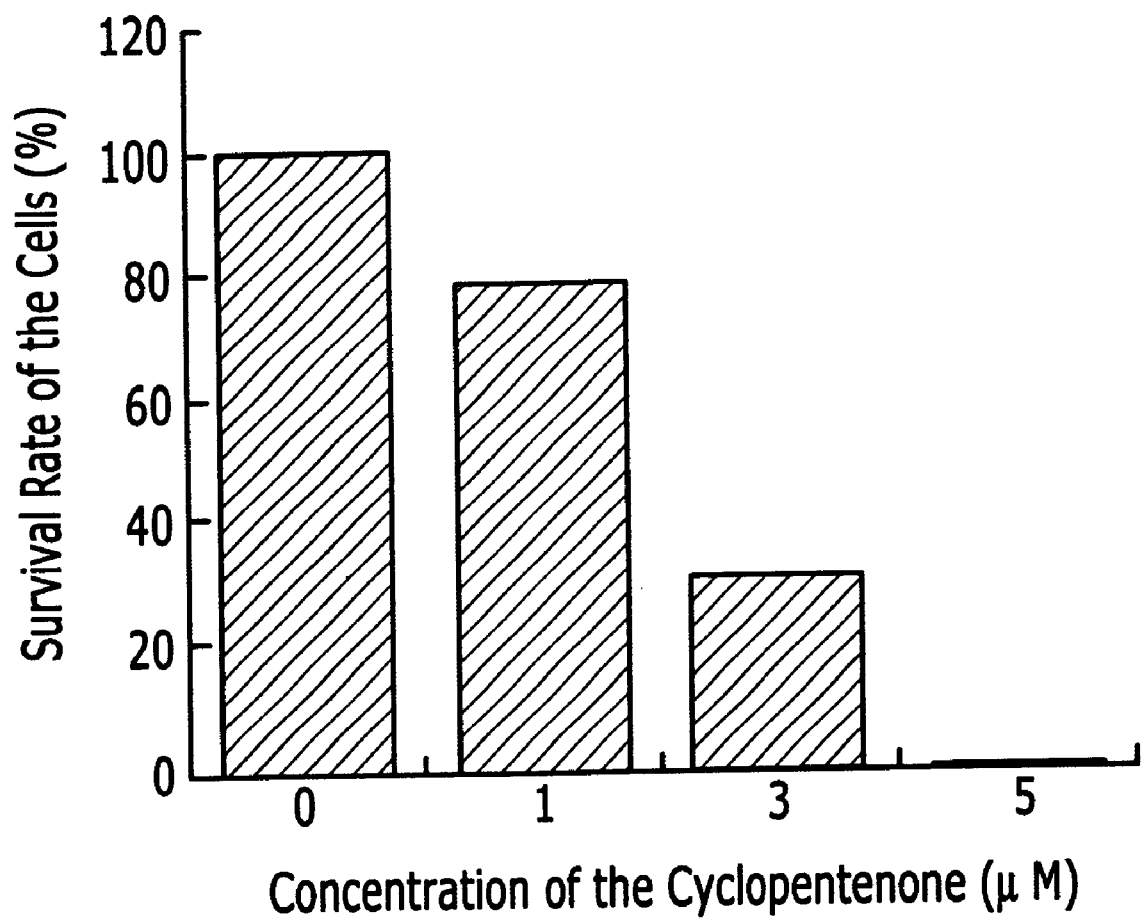
FIG. 4 is a graph showing the relation between the concentration of the cyclopentenone and the survival rate when H9-3B cells are used.

The result was that, in both cells, the survival rate of the cells significantly decreased by addition of 3 μM of the cyclopentenone and, in the case of addition of 5 μM of the cyclopentenone, the survival rate of the cells further decreased. Thus, as compared with Example 5-(1), the cyclopentenone showed an anti-HIV action. The result is shown in FIG. 3 and in FIG. 4. Thus, FIG. 3 and FIG. 4 are the graphs showing the relation between the concentration of the cyclopentenone added and the survival rate of the cells in which abscissa is the concentration (μM) of the cyclopentenone added While ordinate is the survival rate (%) of the cells after incubating for three days. FIG. 3 is the result when CEM-3B were used while FIG. 4 is the result when H9-3B were used.

Example 6

Concentration of the p24 antigen contained in the supernatant liquid of the culture after incubation for three days in the case of Example 5-(2) was measured. The result was that the concentration of p24 decreased corresponding to the centration of the cyclopentenone added thereto whereupon the anti-HIV action was noted. The result is shown in Table 10. In Table 10, the figures in parentheses are the ratio of each of the supernatant liquid of the cell cultures (when none of the cyclopentenone was added) to the concentration of p24 expressed in terms of %.

TABLE 10

| Concentration of the Cyclopentenone | Concentration (ng/ml) of p24 in Supernatant Liquid of the cell cultures | |
|---|---|---|
| (μM) | CEM-3B | H9-3B |
| 0 | 280 (100%) | 210 (100%) |
| 1 | 232 (83%) | 203 (97%) |
| 3 | 176 (63%) | 157 (75%) |
| 5 | 175 (63%) | 148 (70%) |

Example 7

Vero cells (ATCC CCL-81) was suspended in an Eagle's MEM containing 10% of fetal bovine serum until the cell concentration became $5 \times 10^4$ cells/100 μl, the suspension was placed in a 96-well microtiter plate to such an extent that 100 μl of the cell suspension was poured into each well and incubated overnight at 37° C. in the presence of 5% carbon dioxide gas and the Vero cells in a state of monolayers were prepared.

An Eagle's MEM medium to which the cyclopentenone was added to make its final concentration 0, 5, 10, 20 or 40 μM was added to the cells and incubation was conducted at 37° C. for seven hours in the presence of 5% of carbon dioxide gas.

After completion of the incubation, the medium was removed, washing with PBS was conducted twice, then Japanese encephalitis virus (JEV Ja0Ar-363-70 strain) was inoculated to an extent of $4.9 \times 10^2$ pfu/ml, incubation was conducted at 37° C. for 30 hours in the presence of 5% of carbon dioxide gas, the cells were fixed by ethanol and a focus counting was conducted by means of a focus counting by a PAP method [Arch. Virol., volume 86, pages 129–135 (1985)].

The result was that, in the sections to which 40 μM of the cyclopentenone was added, the numbers of the focus apparently decreased as compared with the control in which none of the cyclopentenone was added. The result is given in Table 11. Incidentally, the cells were not eliminated but adhered in each of the to section to which the cyclopentenone was added.

TABLE 11

| Cyclopentenone Concentration (μM) | pfu/ml |
|---|---|
| 0 | $3.0 \times 10^7$ |
| 10 | $1.6 \times 10^7$ |
| 20 | $2.1 \times 10^7$ |
| 40 | $4.9 \times 10^6$ |

(2) Vero cells which were incubated in a 24-well microplate useing an Eagle's MEM containing 10% of fetal bovine serum in the presence of 5% of carbon dioxide gas at 37° C. until the monolayers were resulted were washed with PBS, infected by $4.9 \times 10^2$ pfu/ml of Japanese encephalitis virus (JEV Ja0Ar-363-70 strain) and incubated at 37° C. for 90 minutes.

After the incubation, the cells were washed with PBS and incubation in an MEM to which the cyclopentenone was added to make its final concentration 0, 5, 10, 20 or 40 μM.

The superatant liquid of the infected cells was collected after 0, 1, 2 and 3 day(s) and the titer of the virus were determined means of the focus counting by a PAP method [J. Clin. Microbiol., volume 28, pages 1308–1313 (1990)].

The result was that, in the sections to which 10 μM or more of the cyclopentenone was added, the numbers of the focus apparently decreased as compared with the control in which none of the cyclopentenone was added. The result is given in Table 12. Incidentally, the cells were not eliminated but adhered in each of the sections to which the cyclopentenone was added.

TABLE 12

| Concentration of the Cyclopentenone (μM) | Days after Inoculation of Virus | | |
|---|---|---|---|
| | 1 pfu/ml | 2 pfu/ml | 3 pfu/ml |
| 0 | $6.0 \times 10^3$ | $5.6 \times 10^6$ | $1.1 \times 10^7$ |
| 10 | $6.0 \times 10^3$ | $2.4 \times 10^6$ | $4.4 \times 10^6$ |
| 20 | $6.4 \times 10^3$ | $1.9 \times 10^6$ | $3.0 \times 10^6$ |
| 40 | 0 | 0 | 0 |

From the above result for Example 7-(1) and (2), it is apparent that the cyclopentenone exhibits an antiviral activity to the Japanese encephalitis virus. Incidentally, the Japanese encephalitis virus belongs to a species of the same type as the hepatitis C virus does and, under the present circumstances where incubation of the hepatitis C in vitro has not been established yet, the Japanese encephalitis virus is used as a model of the hepatitis C virus. Consequently, the cyclopentenone is effective as a therapeutic agent for the hepatitis C as well.

In the meanwhile, the same result was obtained for the (−)-cyclopentenone and the (+)-cyclopentenone as well.

Example 8

When a female who was diagnosed to be hepatitis C five year ago and showed no improvements in hepatic functions where both GOT and GPT were around 150 in spite of a treatment with interferon and Minofagen Strong took the beverage which was prepared according to Example 13 at the dose of 50 ml (containing 2 mg of the cyclopentenone) for two months, both GOT and GPT were improved to 80.

When she took it for additional one month, both GOT and GPT became 30 whereupon a significant improvement in hepatic function was noted.

Example 9

Hair on the back of mice of ICR strain (purchased from Nippon SLC; seven weeks age; female) was shaved and DMBA (dimethylbenzanthracene) as an initiator in a form of a solution in acetone was applied thereto at the dose of 50 μg/mouse. After one week, TPA (12-o-tetrasecanoylphorbol 13-acetate) as a promoter in a form of a solution in acetone at the dose of 1 μg/mouse was applied twice a week to the site where the initiator was applied until the completion of the test while 80% ethanolic solution of the cyclopentenone or 80% ethanol (control) was applied one hour before each application of TPA whereupon the anti-carcinogenic action to carcinogenesis caused by a two-stage carcinogenesis on skin was observed for 20 weeks.

Figure 5:
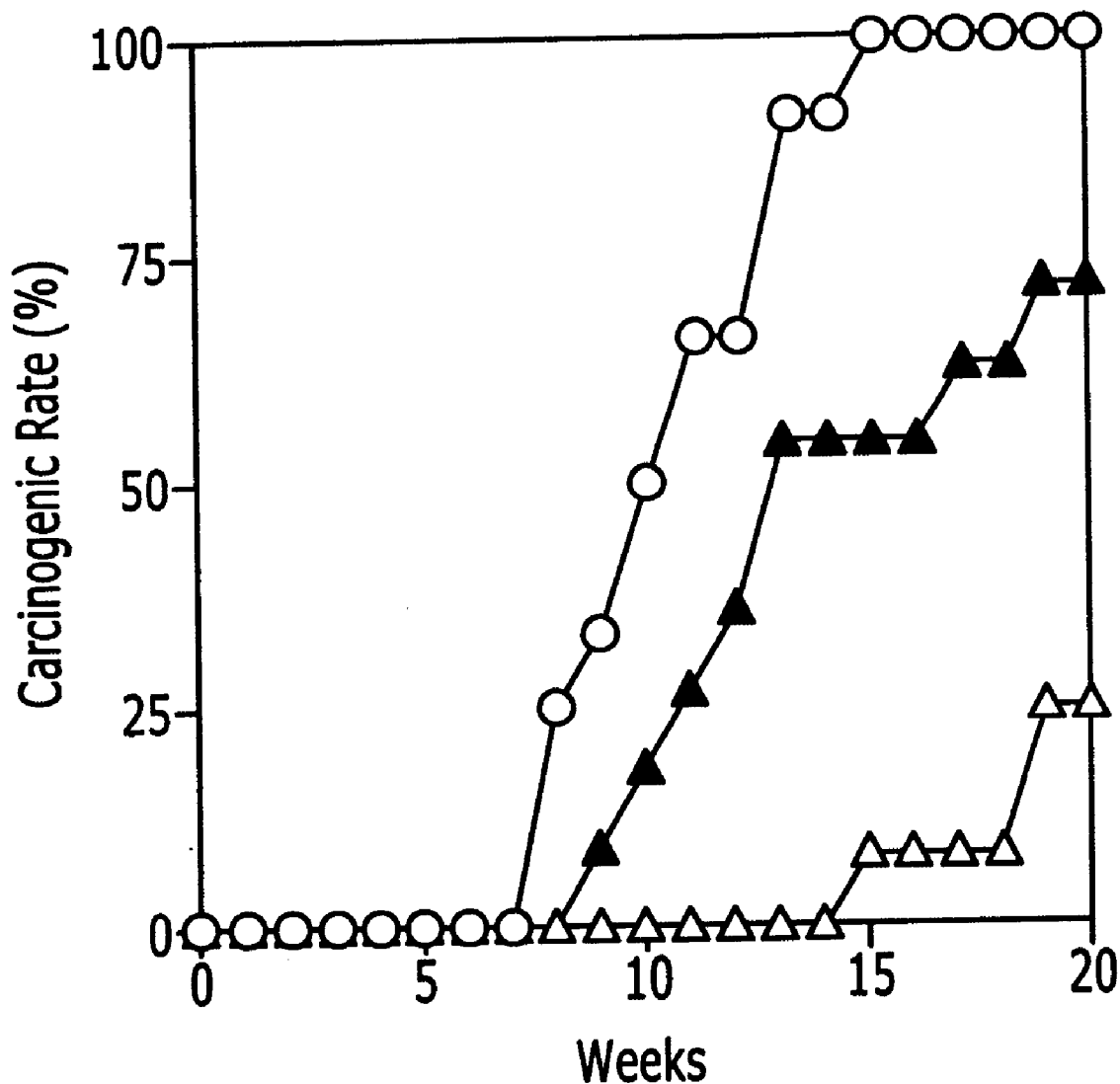
FIG. 5 is a graph showing an inhibiting action of the cyclopentenone against carcinogenicity.

The control group (a group applied with a vehicle only) showed a carcinogenic rate of 100% (12 mice out of 12) within 15 weeks while the cyclopentenone strongly suppressed the carcinogenesis and the carcinogenic rate of the mice administered with 2.5 mg within 15 weeks was 8.3% (1 mouse out of 12) and that within and after 19 weeks was 25% (3 mice out of 12). The result is given in FIG. 5. Thus, FIG. 5 is a graph showing the anti-carcinogenic action of the cyclopentenone in which ordinate is a carcinogenic rate while abscissa is time (weeks). In the graph, open triangles, black triangles and open circles stand for a group treated with 2.5 mg of the cyclopentenone per mouse (12 mice in total), a group treated with 0.8 mg of the cyclopentenone per mouse (11 mice in total) and a control group (12 mice in total), respectively.

Incidentally, in the anti-inflammatory test of TPA in conchae of mice, the cyclopentenone showed no anti-inflammatory activity by application of 2.5 mg (per mouse) to concha of the mouse.

To sum up, the cyclopentenone showed an anti-promoter action in a two-stage chemical carcinogenesis. Heated product of glucuronic acid containing the cyclopentenone, the (−)-cyclopentenone and the (+)-cyclopentenone showed the same result as well.

Example 10

Injection Preparations (1) Cyclopentenone was added to a physiological saline solution (as listed in the Japanese Pharmacopoeia) in a concentration of 1% to prepare an injection preparation.

(2) (−)-cyclopentenone and glycyrrhizic acid were added to a physiological saline solution (the same as above) in concentrations of 0.5% and 0.1%, respectively, to prepare an injection preparation.

Example 11

Tablets (1) A tablet containing 10 mg of cyclopentenone and an appropriate amount of microcrystalline cellulose was prepared and coated with sugar to manufacture a tablet preparation.

(2) A tablet containing 0.1 mg of (+)-cyclopentenone, 10 mg of dipotassium glycyrrhizinate and an appropriate amount of microcrystalline cellulose was prepared and coated with sugar to manufacture a tablet preparation.

Example 12

Ointment

| | |
|---|---|
| cyclopentenone | 1 g |
| Absorption ointment (as listed in the Japanese Pharmacopoeia) | 99 g |

First, cyclopentenone was well kneaded with a small amount of absorption ointment and then the residual absorption ointment was gradually added thereto and kneaded therewith until homogeneity was resulted to prepare an ointment preparation.

This ointment was applied to the affected part for four to five times a day.

Example 13

(1) Pectin (Pomosin Pectin LM-13CG; manufactured by Hercules) (5 kg) was added to 100 liters of tap water and the mixture was heated from the liquid temperature of 28° C. to 120° C. by means of blowing steam thereinto during 35 minutes, kept at 120° C. for five hours with stirring and cooled to prepare 135 liters of cooled mixture. To this were added 1.35 kg of Celite #545 (manufactured by Celite) and 1.35 kg of Silica #600-S (manufactured by Chuo Silica) as filter aids and filtration was conducted using a compact filter (6-inch filter paper in 16 stages; ADVANTEC #327) pre-coated with 0.1 kg of Celite #545 and 0.1 kg of Silica #600-S. The resulting filtrate was subjected to a continuous instant heating treatment (at 98° C. for 60 seconds) using a plate heater (manufactured by Nichihan Seisakusho) followed by cooling to prepare 150 liters of heat-treated pectin solution containing the cyclopentenone.

Said heat-treated pectin solution containing the cyclopentenone had pH of about 3.5, acidity of 6.2 ml and sugar degree of 5.8 Brix %. Incidentally, pH was measured byapH meter, acidity was expressed in terms of the amount (ml) of 0.1N NaOH used for neutralizing to pH 7.0 and sugar degree was measured by a Brix saccharometer.

(2) Beverage was prepared according to the following formulation.

| | |
|---|---|
| Fructose-Glucose-Liquid Sugar | 5.00% |
| Sugar | 4.00% |
| Acidic agent | 1.20% |
| Perfumes | 0.30% |
| Cyclopentenone-containing material | 0.5% |
| Pure water | balance |
| Total | 100.00% |

The heat-treated pectin solution containing the cyclopentenone mentioned in Example 13-(1) was used as the cyclopentenone-containing material and its amount calculated on a solid basis was added. This beverage (100 ml) contains 4 mg of the cyclopentenone.

MERIT OF THE INVENTION

The present invention offers an antiviral agent containing a compound having a function of inducing a resistance to virus to cells and a function of selectively killing the virus-infected cells such as the cyclopentenone, an optically active substance or a salt thereof as an effective component.

The antiviral agent of the present invention selectively kills the virus-infected cells and gives a resistance to virus to normal cells which are not infected by virus and, as a result of synergistic action thereof, it is an antiviral agent which is extremely useful for the therapy of intractable viral diseases such as AIDS and hepatitis C and also for the improvement in symptoms thereof. In addition, the present invention offer a pharmaceutical agent containing the cyclopentenone, an optically active substance or a salt thereof which exhibits various physiological activities such as an action of improving the hepatic function, an action of inducing the heat shock proteins, an action of preventing the viral carcinogenesis and an anti-promoter action. Said pharmaceutical agent affords a drug which is useful for maintaining the homeostasis of living body, particularly maintaining the health of stomach and intestine.

The present invention further offers an antiviral food and antiviral beverage containing a compound having a function of inducing a resistance to virus to cells and a function of selectively killing the virus-infected cells such as the cyclopentenone, an optically active substance or a salt thereof as an effective component. Such food and beverage are useful as food and beverage for improving the symptoms of various diseases caused by virus. In addition, the present invention offers food and beverage containing the cyclopentenone, an optically active substance or a salt thereof which exhibits physiological activity such as an action of improving the hepatic function, an action of inducing the heat shock proteins, an action of preventing the viral carcinogenesis and an anti-promoter action and said food and beverage are useful for maintaining the homeostasis of living body, particularly maintaining the health of stomach and intestine.

What is claimed is:

1. A method of inducing a resistance to a virus into a cell, the method comprising administering a compound selected from the group consisting of 4,5-dihydroxy-2-cyclopenten-1-one of formula (I):

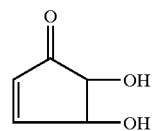

an optical isomer of the 4,5-dihydroxy-2-cyclopenten-1-one of the formula (I), and a mixture thereof, as an effective component.

2. The method according to claim 1, wherein the cell is of a human being, an animal or a plant.

3. The method according to claim 2, wherein the animal is a domestic animal, a fish or a shrimp.

4. The method according to claim 3, wherein the domestic animal is a domestic fowl.

5. The method according to claim 1, wherein the virus is human AIDS virus or hepatitis C virus.

6. A method of selectively killing a cell infected by a virus comprising administering a compound selected from the group consisting of 4,5-dihydroxy-2-cyclopenten-1-one of formula (I):

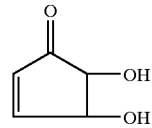

an optical isomer of the 4,5-dihydroxy-2-cyclopenten-1-one of the formula (I), and a mixture thereof, as an effective component.

7. The method according to claim 6, wherein the cell is of a human being, an animal or a plant.

8. The method according to claim 7, wherein the animal is a domestic animal, a fish or a shrimp.

9. The method according to claim 8, wherein the domestic animal is a domestic fowl.

10. The method according to claim 6, wherein the virus is human AIDS virus or hepatitis C virus.

* * * * *